United States Patent [19]
Epstein et al.

[11] Patent Number: 5,250,163
[45] Date of Patent: * Oct. 5, 1993

[54] PROTON CONCENTRATION SENSOR/MODULATOR FOR SULFONATED AND HYDROXYLATED POLYANILINE ELECTRODES

[75] Inventors: Arthur J. Epstein, Bexley, Ohio; Jiang Yue, Cambridge, Mass.; David R. Burley, Kinnelon, N.J.

[73] Assignee: The Ohio State University Research Foundation, Columbus, Ohio

[*] Notice: The portion of the term of this patent subsequent to Aug. 11, 2009 has been disclaimed.

[21] Appl. No.: 800,363

[22] Filed: Nov. 27, 1991

[51] Int. Cl.$^5$ .............................................. G01N 27/26
[52] U.S. Cl. .............................. 204/153.21; 204/433; 204/435
[58] Field of Search ...................... 204/153.21, 153.12, 204/403, 416, 418, 412, 433, 435; 252/500

[56] References Cited

U.S. PATENT DOCUMENTS 5,137,991 8/1992 Epstein et al. ...................... 252/511

Primary Examiner—John Niebling
Assistant Examiner—Bruce F. Bell
Attorney, Agent, or Firm—Mueller and Smith

[57] ABSTRACT

Broadly, the present invention takes advantage of the ability of self-protonated sulfonated polyaniline (SPAN) to sense and/or modulate pH of a medium in the vicinity of a SPAN electrode. Accordingly, one aspect of the present invention is directed to a method for sensing pH of a medium in the vicinity of a sensing electrode wherein a SPAN electrode and a counter-electrode are placed in a medium and an indicia of said SAN correlative with the pH of said medium is monitored. As another aspect of the present invention, the pH of a medium in the vicinity of a sensing electrode is modulated by placing a SPAN electrode in the medium and applying a voltage to the electrode to controllably emit or absorb protons from said electrode to modulate the pH of the medium in the vicinity of the electrode. As a further aspect of the present invention, the activity/state of a biosensor/catalyst is sensed for the activity/state correlative with pH. As a further aspect of the present invention, the activity/state of a biosensor/catalyst, where the activity/state is correlative with pH, is controlled by associating the biosensor/catalyst with a SPAN electrode in contact with a medium containing said biosensor/catalyst, and applying a voltage to said electrode to controllably emit or absorb protons from said electrode to control the activity/state of said biosensor/catalyst.

25 Claims, 4 Drawing Sheets

PROTON CONCENTRATION SENSOR/MODULATOR FOR SULFONATED AND HYDROXYLATED POLYANILINE ELECTRODES

This invention was made with government support under Grant No. N00014-86-K-0766 awarded by the Office of Naval Research. The government has certain rights in the invention.

CROSS-REFERENCE TO RELATED APPLICATIONS

The present invention is cross-referenced to Epstein and Yue U.S. Pat. Nos. 5,137,991, 5,093,439, 4,556,623, 5,135,696, 5,164,465, and 5,159,031, the disclosures of which are expressly incorporated herein by reference.

BACKGROUND OF THE INVENTION

The present invention relates to hydroxylated polyaniline and sulfonated polyaniline electrically-conductive compositions and more particularly to their use in sensing and modulating pH of a medium in association therewith.

Polyaniline is a family of polymers that has been under intensive study recently because the electronic and optical properties of the polymers can be modified through variations of either the number of protons, the number of electrons, or both. The polyaniline polymer can occur in several general forms, including the so-called reduced form (leucoemeraldine base), possessing the general formula:

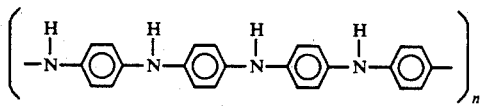

the partially oxidized or so-called emeraldine base form, of the general formula:

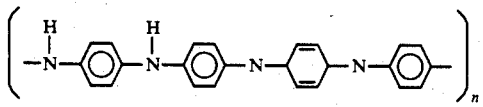

and the fully oxidized or so-called pernigraniline form, of the general formula:

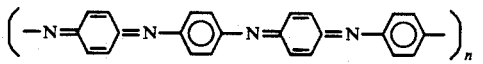

In practice, polyaniline generally exists as a mixture of the several forms with a general formula of:

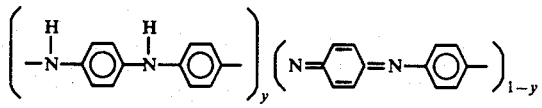

When $0 \leq y \leq 1$, the polyaniline polymers are referred to as poly(paraphenyleneammeimines) in which the oxidation state of the polymer continuously increases with decreasing values of y. The fully reduced poly(paraphenyleneamine) is referred to as leucoemeraldine, having the repeating units indicated above corresponding to a value of $y=1$. The fully oxidized poly(paraphenyleneimine) is referred to as pernigraniline, of repeat unit shown above corresponding to a value of $y=0$. The partially oxidized poly(paraphenyleneamineimine), with y in the range of greater than or equal to 0.35 and less than or equal to 0.65, is termed emeraldine, though the name "emeraldine" often is focused on the compositon where y is equal to (or approximately equal to) 0.5. Thus, the terms "leucoemeraldine", "emeraldine", and "pernigraniline" refer to different oxidation states of polyaniline. Each oxidation state can exist in the form of its base or in its protonated (salt) form by treatment of the base with an acid.

The use of the terms "protonated" and "partially protonated" herein includes, but is not limited to, the addition of hydrogen ions to the polymer by, for example, a pretonic acid, such as a mineral acid and/or organic acids. The use of the terms "protonated" and "partially protonated" herein also includes pseudo-protonation, wherein a cadon such as, but not limited to, a metal ion, $M^+$, is introduced into the polymer. For example, "50%" protonadon of emeraldine formally leads to a composition of the formula:

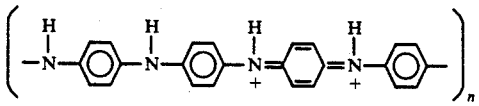

which may be written as:

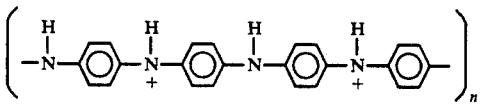

Formally, the degree of protonation may vary from a ratio of $[H^+]/[-N=]=0$ to a ratio of $[H^+]/[-N=]=1$. Protonation or partial protonation at the amine (—NH) sites also may occur.

The electrical and optical properties of the polyaniline polymers vary with the different oxidation states and the different forms. For example, the leucoemeraldine base, emeraldine base, and pernigraniline base forms of the polymer are electrically insulating while the emeraldine salt (protonated) form of the polymer is conductive. Protonation of emeraldine base by aqueous 1M HCl to produce the corresponding salt brings about an increase in electrical conductivity by a factor of $10^{12}$. Deprotonation occurs reversibly in aqueous base or upon exposure to vapors which form aqueous bases, such as, for example, ammonia. The emeraldine salt form also can be achieved by electrochemical oxidation of the leucoemeraldine base polymer or electrochemical reduction of the pernigraniline base polymer in the presence of an electrolyte of the appropriate pH. The rate of the electrochemical reversibility is very rapid. Solid polyaniline can be switched between conducting, protonated, and nonconducting states at a rate of approximately $10^5$ Hz for electrolytes in solution and even faster with solid electrolytes. (E. Paul, *J. Phys. Chem.*, 1985, 89, 1441–1447).

The rate of electrochemical reversibility also is controlled by the thickness of the film, thin films exhibiting a faster rate than thick films. Polyaniline, then, can be reversibly switched from an insulating to a conducting form as a function of protonation level (controlled by ion insertion) and oxidation state (controlled by electrochemical potential). Thus, in contrast to, for example polypyrrole, polyaniline can be turned "on" by either an negative or a positive shift of the electrochemical potential, because polyaniline films essentially are insulating at sufficiently negative (approximately 0.00 V vs SCE) or positive (+0.7 V vs SCE) electrochemical potentials. Polyaniline also can then be turned "off" by an opposite shift of the electrochemical potential.

The conductivity of polyaniline is known to span 12 orders of magnitude and to be sensitive to pH and other chemical parameters. It is well-known that the resistance of films of both the emeraldine base and 50% protonated emeraldine hydrochloride polymer decrease by a factor of approximately 3-4 when exposed to water vapor. The resistance increases only very slowly on removing the water vapor under dynamic vacuum. The polyaniline polymer exhibits conductivities of approximately 1 to 200 Siemens per centimeter (S/cm) when approximately half of its nitrogen atoms are protonated. Electrically conductive polyaniline salts, such as fully protonated emeraldine salt $[(-C_6H_4-NH-C_6-H_4-NH^+)-Cl-]_x$, have high conductivity ($10^{-4}$ to $10^{+2}$ S/cm) and high dielectric constants (20 to 2,000), and have a dielectric loss tangent of from below $10^{-3}$ to approximately $10^1$. Dielectric loss values are obtained in the prior art by, for example, carbon filled polymers, but these losses are not as large nor as readily controlled as those observed for polyaniline.

While the preparation of polyaniline polymers and the protonated derivatives thereof are known in the art, it is novel to prepare sulfonated polyaniline compositions which are capable of being "self-protonated" or "self-doped", as disclosed in the related applications cited above. Use of the terms "self-protonated" and "self-doped" herein includes, but is not limited to, the reorganization of hydrogen ions on the polymer chain. For example, self-doping or self-protonation of a polyaniline base polymer leads to a polyaniline salt polymer and a reorganization of the electronic structure which then forms a polaronic metal. The conductivity of such polaronic metal is independent of external protonation.

BROAD STATEMENT OF THE INVENTION

Broadly, the present invention takes advantage of the ability of self-protonated sulfonated polyaniline (SPAN) to sense and/or modulate pH of a medium in the vicinity of a SPAN electrode. Accordingly, one aspect of the present invention is directed to a method for sensing pH of a medium in the vicinity of a sensing electrode wherein a SPAN electrode and a counterelectrode are placed in a medium and an indicia of said SPAN correlative with the pH of said medium is monitored. Preferably, the SPAN indicia is one or more of electrical potential relative to a reference electrode, conductivity of the SPAN electrode, or color of the SPAN electrode. It is withing the scope of the sensing embodiment of the present invention to control one of the SPAN indicia by varying the pH of the medium. For this SPAN electrode indicia to be effective, nevertheless, the SPAN electrode would be "sensing" the pH of the medium. As another aspect of the present invention, the pH of a medium in the vicinity of a sensing electrode is modulated by placing a SPAN electrode in the medium and applying a voltage to the electrode to controllably emit or absorb protons from said electrode to modulate the pH of the medium in the vicinity of the electrode. As a further aspect of the present invention, the activity/state of a biosensor/catalyst is sensed for the activity/state correlative with pH. This aspect of the present invention comprises associating the biosensor/catalyst with the SPAN electrode in contact with a medium (e.g., the medium containing the biosensor/catalyst and/or the biosensor/catalyst being reacted with the SPAN and/or the biosensor being entrained by the SPAN) and monitoring an indicia of said SPAN correlative with pH which is correlative with the activity/state of one or more of said biosensor/catalyst, a substrate affected by said biosensor/catalyst, or a substrate which affects said biosensor/catalyst. Again, the SPAN indicia is one or more of electrical potential relative to a reference electrode, conductivity, or color. As a further aspect of the present invention, the activity/state of a biosensor/catalyst, where the activity/state is correlative with pH, is controlled by associating the biosensor/catalyst with a SPAN electrode in contact with a medium (e.g., the medium containing the biosensor/catalyst and/or the biosensor/catalyst being reacted with the SPAN and/or the biosensor being entrained by the SPAN), and applying a voltage to said electrode to controllably emit or absorb protons from said electrode to control the activity/state of said biosensor/catalyst. For present purposes, "activity/state" means "activity or state" and "biosensor/catalyst" means "biosensor or catalyst", in conventional fashion.

Additionally, a substituted polyaniline polymer where —OH replaces —SO$_3$ also is expected to function as does the SPAN electrode, though its E ½ (versus pH) does not behave theoretically, as can be seen by reference to FIG. 1. Nonetheless, hydroxylated polyaniline polymers are included within the disclosure of the present invention, even though most of the description will be by reference to SPAN electrodes, which is by way of illustration and not limitation.

DETAILED DESCRIPTION OF THE INVENTION

Figure 1:
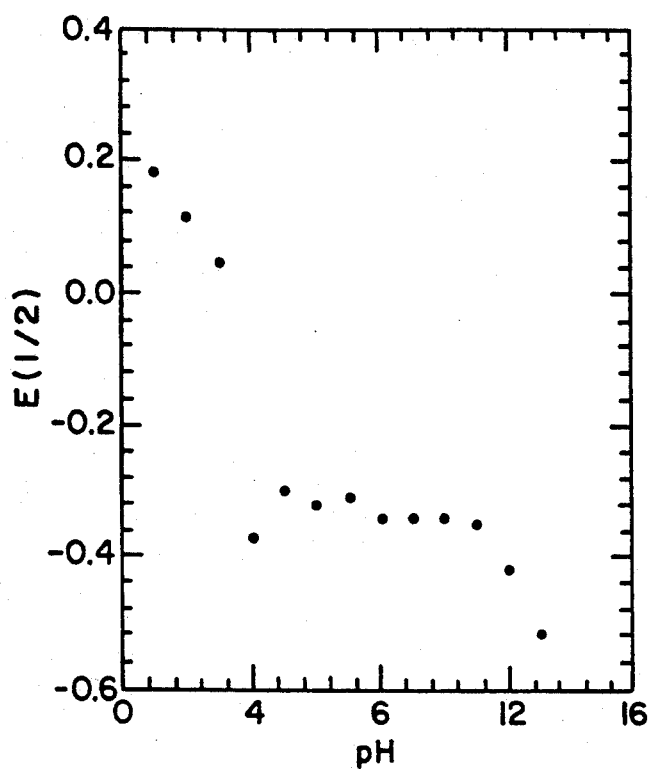
FIG. 1 plots potention, E½, as a function of pH for the first oxidation wave for a hydroxylated polyaniline electrode versus a Ag/AgCl reference electrode.

Self-protonated sulfonated polyaniline (SPAN) compositions useful in practice of the present invention are disclosed in the applications cross-referenced above. Further information can be found in the following publications, the disclosures of which are expressly incorporated herein by reference: MacDiarmid et al, "Polyanilines: Synthesis, Chemistry and Processing", *New Aspects of Organic Chemistry II, Proceedings of the Fifth International Kyoto Conference on New Aspects of Organic Chemistry*, VCH (Weinheim) and Kodansha (Tokyo), Co-publishers (Spring 1992); Yue et al, "Effect of Sulfonic Acid Group on Polyaniline Backbone" *JACS*, 113, 2665-2671 (1991); Epstein et al, "Novel Concepts in Electronic Polymers: Polyaniline and its Derivatives", *Die Makronwiekulare Chemie*, Symposium Volume, Proceedings, International Symposium on Specialty Polymers, Singapore 7-9 November 1990; Epstein et al., "The Chemical Control of Processability, Electromagnetic Response and Other Properties of Polyanilines and Their Applications to Technologies", *Proc. Society of Plastics Engineers*, Annual Technical Conference, Montreal, Canada, 755-759 (5-9 May 1991); Yue et al, "Synthesis of Sels Doped Conducting Polyaniline", *JACS*, 112, 2800-2801 (1990); and Yue et al, "Comparison of Different Synthetic Routes for Sulfonation of Polyaniline", *Polymer*, to be published in 1992), the disclosures of which are expressly incorporated herein by reference.

Such SPAN materials can be represented by formula I (where for the sake of clarity only, the structure shown in formula I is in the non self-protonated form):

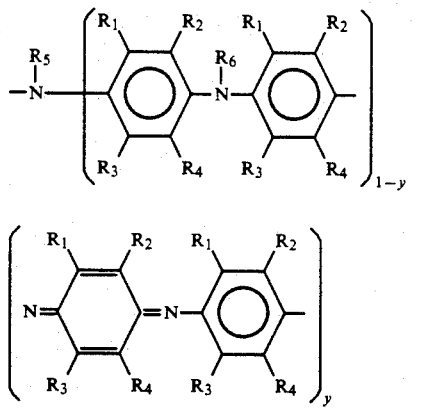

(I)

wherein $0 \leq y \leq 1$; $R_1$, $R_2$, $R_3$, $R_4$, $R_5$, and $R_6$ independently are selected from the group consisting of —H, —$SO_3$—, —$SO_3H$, —$R_7SO_3$—, —$OCH_3$, —$CH_3$, —$C_2H_5$, —F, —Cl, —Br, —I, —$(NR_7)_2$, —$NHCOR_7$, —OH, —$R_7OH$, —O—, —$SR_7$, —$OR_7$, —$OCR_7$, —$NO_2$, —COOH, —$COOR_7$, —CHO, and —CN, wherein $R_7$ is a $C_1$-$C_8$ alkyl, aryl, or aralkyl group.

For the SPAN material, the fraction of rings containing at least one $R_1$, $R_2$, $R_3$, or $R_4$ group being an —$SO_3$—, —$SO_3H$, —$R_7SO_3$—, or —$R_7SO_3H$ group, can be varied from a few percent (e.g. 20%) to one hundred percent. It is within the contemplated scope of the present invention that the —$R_7SO_3$— and —$R_7SO_3H$ substituents can be varied so that the sulfonated polyaniline is soluble in a range of solvents in order to make the sulfonated polyaniline polymer more easily blendable with other polymers and/or more easily cast onto a variety of surfaces. For the hydroxylated polyaniline material, the fraction of rings containing at least one $R_1$, $R_2$, $R_3$, or $R_4$ group being an —OH group or $R_7OH$ (wherein $R_7$ is a $C_1$-$C_8$ alkyl, aryl, or aralkyl group), can be varied similarly. Copolymers, interpolymers, and similar variations of the polyaniline derivatives also can be prepared and used as is necessary, desirable, or convenient.

The solubility of sulfonated polyaniline can be varied by changing the degree of sulfonation (i.e., the sulfonation time and/or temperature in $H_2SO_4(SO_3)$). It is noted that the oxidation state of the polymer (from leucoemeraldine through emeraldine to pernigraniline) and the degree of sulfonation (x) can be independently varied. Here, x is the fraction Of $C_6$ rings which have an —$SO_3$— or an —$SO_3H$ group attached thereto.

When x=0, the polymer does not dissolve in either basic or acidic aqueous solutions. Upon increasing the value of x, the polymer becomes soluble in strongly basic, basic, weakly basic, and eventually in acidic aqueous solutions. This progressive improvement in solubility implies that the polymer becomes soluble in neutral media, particularly $H_2O$, at the appropriate value of x, yielding a water-soluble conducting polymer. The color of soluble sulfonated polyaniline in acidic solution is green, indicating it is the conducting salt form.

The solubility of polyaniline is increased greatly in basic aqueous solution by the presence Of —$SO_3H$ group on the phenyl rings. This is in contrast with polyaniline which, when washed with basic solutions, converts to the insoluble base form.

Protonation of the emeraldine base polymer leads to the emeraldine salt polymer and a reorganization of the electronic structure to form a polaronic metal. Since benzenesulfonic acid is a strong acid, i.e. about as strong as hydrochloric acid, the sulfonated polyaniline is capable of self-doping. Hence, the conductivity of the sulfonated polyaniline is independent of external protonation.

Being able to dope itself, the sulfonated polyaniline polymer has enhanced optical and electrical response to electrochemical potential as compared with the parent polyaniline polymer. Since the solid-state diffusion of counterions in and out of a polymer during electrochemical processes often is the rate controlling step of the kinetics, it also limits the speed of both optical and electrical response of polymers. In the self-doped conjugated polymer, the counterions are not necessary from the medium. The positive charge introduced into the conjugated $\pi$ electron system of the backbone of the polymer is compensated by the protons migrating out of the polymer, or vice versa, leaving behind the opposite charged counterion. Since the hydrogen ion or proton is the smallest and most mobile ion, proton hopping mechanisms lead to relatively fast doping kinetics as compared to those counterions migrating in or out of the polymer. As a consequence, it is possible to achieve sufficient speed with the SPAN electrode to be useful for a variety of technological applications.

Figure 2:
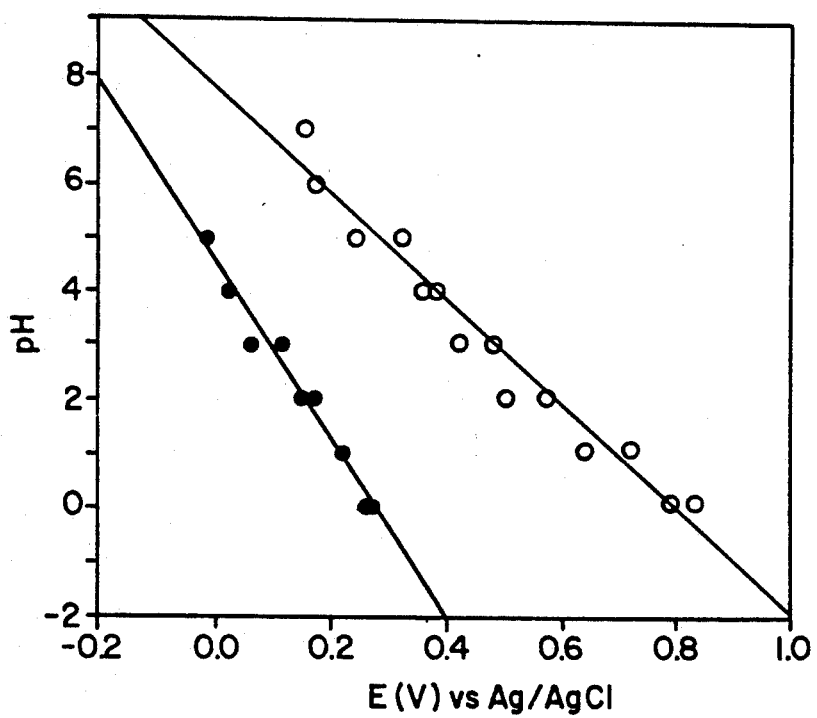
FIG. 2 plots potential as a function of pH for the first and second(◯) oxidation waves for a SPAN electrode versus a Ag/AgCl reference electrode.

Typical cyclic voltammograms of sulfonated polyaniline polymers reveal the two waves, the first oxidation wave varying in its potential as 59 mV/pH and the second oxidation wave varying in its potential as 118 mV/pH. FIG. 2 plots potential of a SPAN electrode versus a Ag/AgCl reference electrode as a function of pH, where the solid dots represent the first oxidation wave and the unfilled dots represent the second oxidation wave. Unique to the self-protonated SPAN electrodes is the ability to control the first oxidation wave.

Typical cyclic voltammograms of the hydroxylated polymers also reveals two oxidation waves, the first varying (on average) at 0.60 mV/pH. FIG. 1 plots potential of an hydroxylated polyaniline electrode versus a Ag/AgCl reference electrode as a function of pH. Unique to hydroxylated polyaniline electrodes is the ability to control the first oxidation wave in the manner shown in FIG. 1.

The SPAN material can be used neat, but preferably is used in a form exhibiting a large surface area. This makes the use of carriers for the SPAN film desirable. Carriers can include, for example, conductive electrodes optionally in screen or other high surface area form, zeolites or similar particulate carriers, or porous substrates such as films. Use of transparent conduction electrodes, such as ITO (indium tin oxide), facilitates optical monitoring of the SPAN and hydroxylated polyaniline electrodes. SPAN also can be entrained in a host polymer. The skilled artisan will appreciate the numerous possibilities that can be envisioned with respect to the form which the SPAN electrode takes for practice of the present invention.

One application is in sensing the pH of a medium into which the SPAN electrode is immersed. Response times in the millisecond range are appropriate for the SPAN electrode, thus making industrial applications even more attractive. This sensing process is non-destructive as no sample is consumed during the pH determination and can be non-intrusive, e.g. by permitting some of the medium to penetrate a membrane area in a wall in a container or other housing for the medium and then contact the SPAN electrode behind the membrane for pH determination.

In general, for an oxidation reaction involving the release of m protons and the transfer of n electrons, the expression for the electrode potential has the form (Bard et al, " Electrochemical Methods, Fundamental & Applications", John Wiley & Sons, New York, New York, 1981):

$$E = E_o + \frac{RT}{nF} \ln \frac{[Ox]}{[Red]} + \frac{RT}{nF} \ln [H^+]^m \quad (II)$$

Hence, the variation of electrode potential with pH is described by the following equation:

$$\frac{\Delta E}{\Delta pH} = -0.059 \frac{m}{n} \quad (III)$$

With the above considerations in mind, the actual evaluation of oxidation reactions involving the release of m protons can be made. The simplest example is the proton hydrogen half-reaction, $$H^+ + e^- \rightarrow \tfrac{1}{2} H_2 \quad (IV)$$

The electrical potential, then, is:

$$E = -0.059 \log \frac{P_{H_2}^{\frac{1}{2}}}{[H^+]} \quad (V)$$

and for the oxygen-water half-reaction:

$$\tfrac{1}{2} O_2 + 2H^+ + 2e^- \rightarrow H_2O \quad (VI)$$

The electrical potential, then, is:

$$E = 1.23 + 0.059 \log\{[H^+] \cdot P_{O_2}^{\frac{1}{2}}\} \quad (VII)$$

Figure 3:
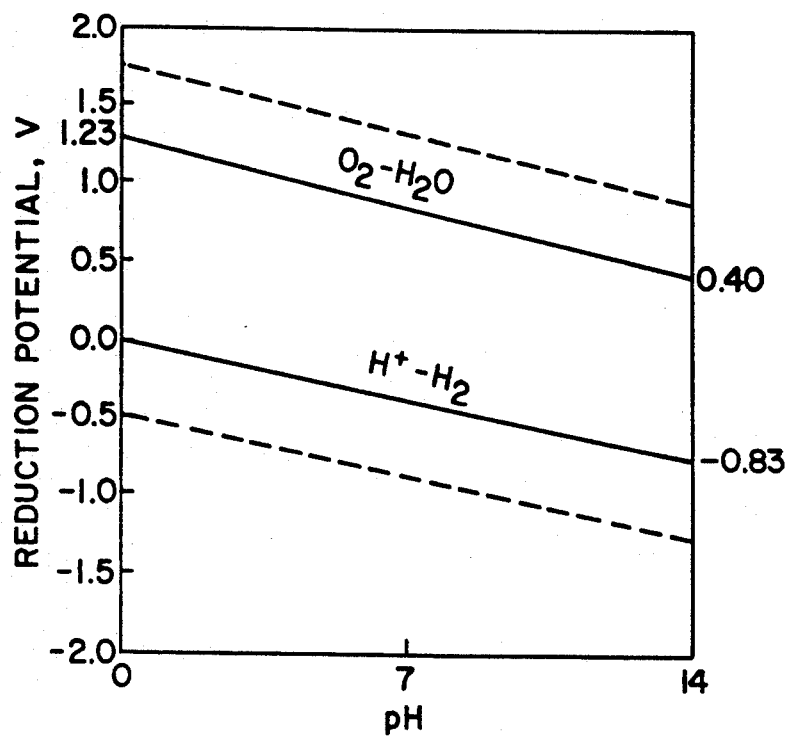
FIG. 3 plots the reduction potentials of the hydrogen and oxygen half-reactions of equations (IV) and (VI) as function of pH.

The potential for these half-reactions are plotted versus pH in FIG. 3 (Jolly, "The Principles of Inorganic Chemistry", Chapter 7, McGraw-Hill Book Co., New York, New York, 1976). Clearly, this plot shows that if one is able to change the pH of the medium, the reactivity of the system is changed. This is one aspect of application of pH modulation based on the SPAN electrode. Standard reduction potentials for systems of biochemical importance at pH=7 can be found, for example, by reference to Mahler et al, "Biological Chemistry", Chapter 3, Harper & Row Publishers, New York, New York, 1971. All of these values (or reactivities) can be changed by changing the pH of the medium.

Another important aspect of using pH modulation of a SPAN electrode is to control the reactivity of enzymes, which are but one class of biosensors, and sense the condition of the electrode. Almost all enzymes are extremely sensitive to pH, their activity being diminished at either side of a relatively narrow range. These effects are due to a combination of three factors: (1) effects of extremes of pH on protein structure, including alterations on the strength and mode of binding of prosthetic groups; (2) effects on the ionization of the substrate; and (3) effects on its binding to the enzyme and on reactivity in catalysis. (Bender, "Catalysis and Enzyme Action", Chapter 3, McGraw-Hill Book Co., New York, New York, 1973) It is the third class that is of concern here since the first two classes usually can be determined independently of the reaction under kinetic study and corrections made for their effects.

Figure 4:
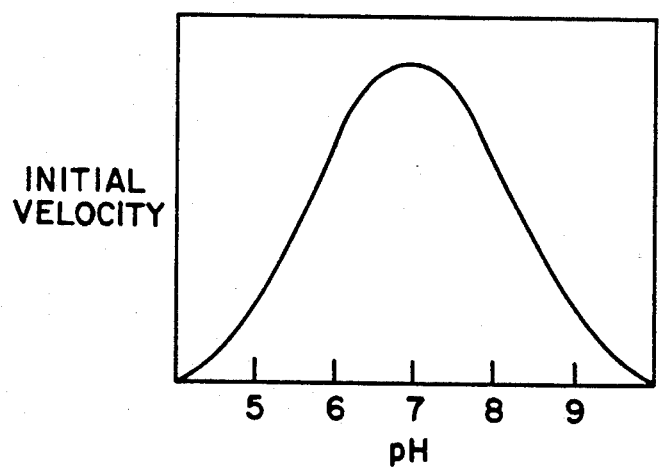
FIG. 4 plots the effect of pH on the rate of enzymatic reactions.

The initial rate of the enzyme reaction proper frequently exhibits three distinct phases as a function of pH as depicted at FIG. 4; a region of pH (at low values) where there is an increase, a region (at high values) where there is a decrease, and an intermediate range (usually around neutrality) where the activity is maximal and leading to a characteristic bell-shaped curve, the location of which, of course, depends upon the individual enzyme or enzyme-like substance. (McGilvery, "Biochemistry—A Functional Approach", Chapter 8, W. B. Saunders Co., Philadelphia, Pa. 1970) By applying the principle shown at FIG. 4, the reactivity of an enzyme can be controlled by the potential modulation of pH for a SPAN electrode in a system.

A possible industrial enzymatic use might be the various sugar producing or reducing enzymes, such as amylase or sucrase. If these enzymes cause protons to be taken up or given up by the media at the same time, then the SPAN electrode would become a specific product detector. The enzyme could be coated onto the electrode or chemically affixed to the SPAN material. For present purposes, an enzyme bound to the SPAN material is "in the vicinity of" for sensing and modulating pH. Also, proton transfer may be direct between the SPAN material and the bound enzyme (though this is presently unknown) and such transfer still is considered within the precepts of the present invention. Further information concerning biosensors can be found in Blum et al, "Biosensor Principles and Applications", Marcel Dekker, Inc., New York, N.Y. (1991), the disclosure of which is expressly incorporated herein by reference.

Regardless of the specific uses, pH modulation with the novel SPAN electrode has certain advantages that make it a potentially useful industrial process. For example, pH change can be easily controlled as micro pH changes are quite within the grasp of the inventive process. Also, the pH change is swift and can go either way, viz up or down. Further, the SPAN electrode provides high charge efficiency, $e-/H^+$. Finally, the SPAN electrodes are easy to fabricate.

Additional applications include food and beverage applications, as well as medical and veterinary medicine applications. For example, sugar detection could be applied to diabetics to control insulin injections. Other in vivo applications that can be envisioned include blood monitoring by pH, enzyme, antibody, or other indicia. Monitoring the brewing and fermenting of beer by pH and enzyme monitoring also is a possible application. In the manner in which biosensors can be utilized, so can inorganic, organic or other catalysts that directly or indirectly take up or emit protons.

The photophysical properties of SPAN in which a color change is experienced in the various oxidation states of the polymer also lead to a number or interesting possible in industrial applications. The voltage required for this change is on the order of 0.5 V and is within the solid state electronic area of application technology. Color generation, or color amplification with respect to voltage, may be useful in signage or other displays, LEDS, television screen manufacture, and the like. Alternatively, a pH indicator or dye could be dispersed in the medium, or otherwise associated with the medium, and pH change sensed or displayed by such indicator in such manner that a flat panel electronic display or flexible high resolution flat panel display can be fabricated. Further, a dye could be associated with the electrode (e.g. by commingling the indicator with SPAN, by the indicator being reacted with SPAN, or by the indicator being reacted with another polymer which then is commingled with SPAN) which dye is color sensitive to potential or conductivity of the electrode, and such dye used to display pH. Dyes or color indicators are well-known to the skilled artisan and can be found by reference to, for example, "Handbook of Chemistry and Physics", pp D-148 and D-149, 66th Edition, The Chemical Rubber Company, Cleveland, Oh. (1985-1986), the disclosure of which is expressly incorporated herein by reference.

Thus, it will be observed that a wide variety of industrial applications are possible using the pH/SPAN interaction disclosed herein as those skilled in the art will appreciate. In this application, all references are expressly incorporated herein by reference.

EXAMPLES

Example 1

About 0.2 mg of SPAN was dissolved into 0.2 nd of 0.1M $NH_4OH$ and cast onto a 0.25 $cm^2$ Pt electrode. The SPAN electrode was dried in air. Then, the electrode was dipped into 1M HCl solution for 30 seconds. After the electrode was rinsed with plenty of water, it was further immersed into 20 ml of deionized water for 30 min. After such procedures, the SPAN electrode was ready to be used.

About 0.2 ml of 1M NaCl with pH of 7.88 was placed on the electrode. By step changing the potential of the electrode while the pH change of the solution was monitored by the pH electrode, the relationship between pH and applied potential can be obtained.

Figure 5:
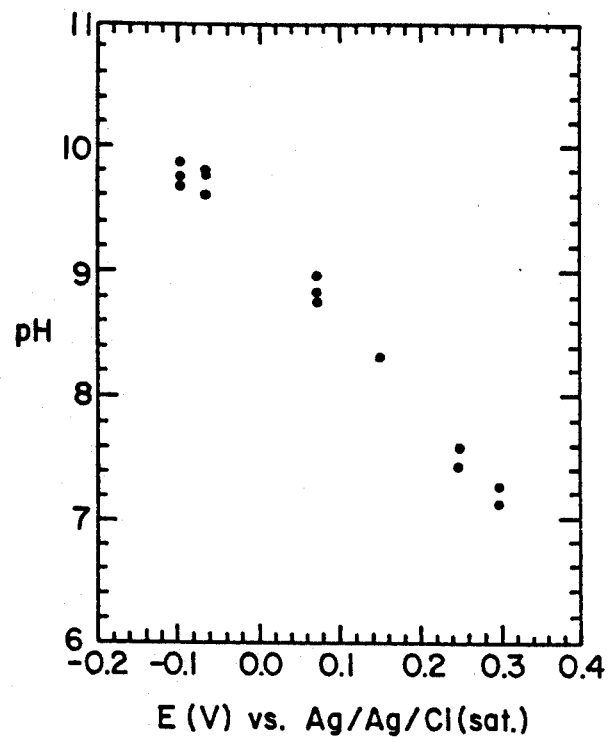
FIG. 5 plots pH as a function of potential for a SPAN coated Pt electrode using 0.2 ml of 1M NaCl with a pH of 7.88 as starring solution as described in Example 1.

The results recorded are displayed at FIG. 5.

Example 2

Figure 6:
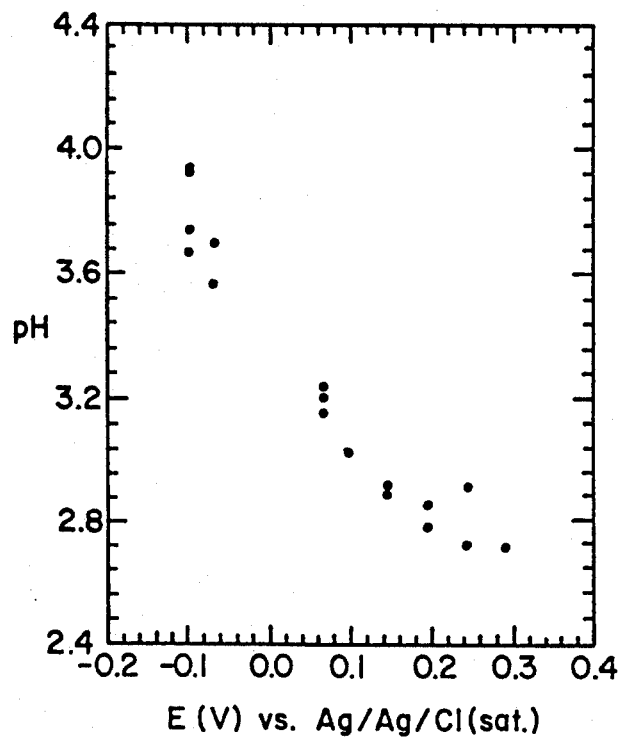
FIG. 6 plots pH as a function of potential for a SPAN coated Pt electrode using 0.2 ml of 0.3M NaCl with a pH of 3.18 as starting solution as described in Example 2.

The procedure reported in Example 1 was repeated, except that 0.3M NaCl with a pH of 3.18 was used as the starting solution. The change of pH as a function of potential is shown at FIG. 6.

Example 3

Figure 7:
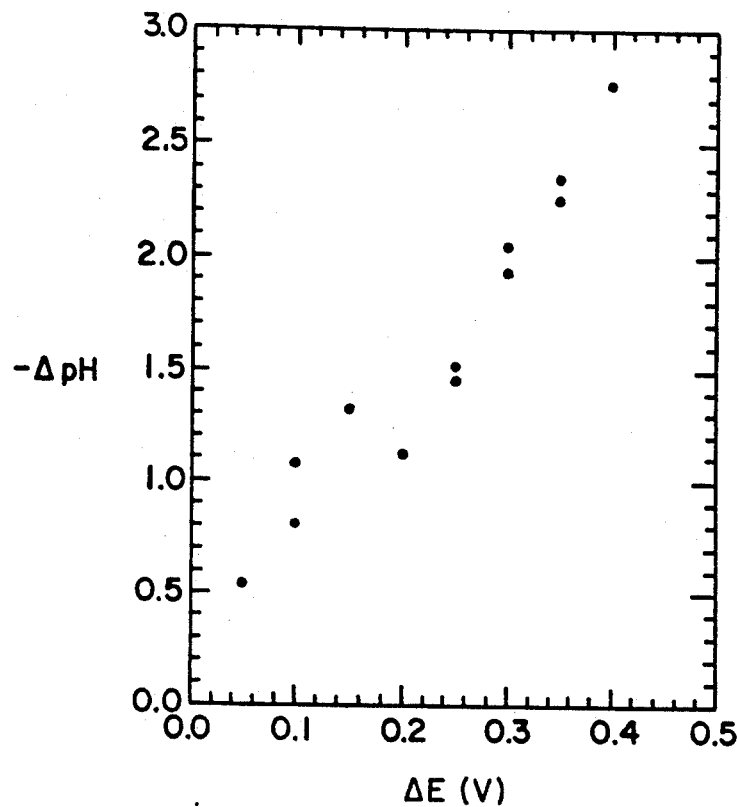
FIG. 7 plots pH as a function of potential for a SPAN coated Pt electrode using 0.2 ml of 1M NaCl with a pH of 5.62 as starting solution as described in Example 3.

The procedure reported in Example 1 was repeated, except that 1M NaCl with a pH of 5.62 was used as the starting solution. The change of pH as a function of change of potential is shown at FIG. 7.

Example 4

Figure 8:
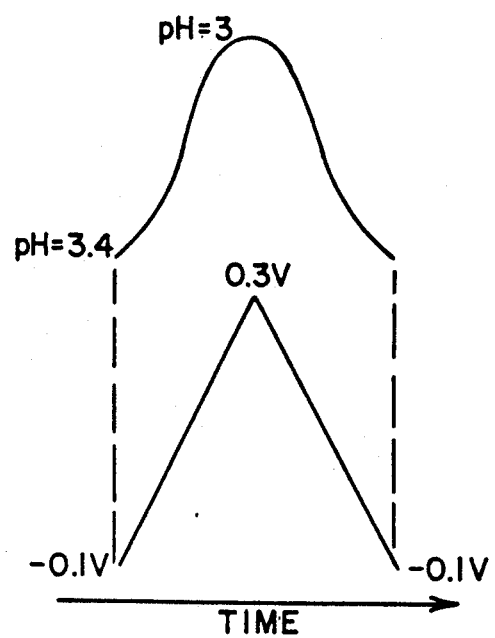
FIG. 8 plots pH as a function of potential, scan rate of potential being 10 mv/S, for a SPAN coated Pt electrode using 0.2 ml of 0.3M NaCl with a pH of 3.18 as starting solution as described in Example 4.

The procedure reported in Example 2 was repeated, except that the potential was changed continuously instead of stepwise. The change of pH as a function of potential is shown at FIG. 8.

Example 5

About 0.2 mg of SPAN was dissolved into 0.2 ml of a 0.1M $NH_4OH$ and cast onto a 0.25 $cm^2$ Pt electrode. The SPAN electrode was dried in air. Then, the electrode was dipped into a 1M HCl solution for 30 seconds. After the electrode was rinsed with plenty of water, it was further immersed into 20 ml of deionized water for 30 min. After such procedures, the SPAN electrode was ready to be used.

Chymotrypsin (an enzyme, 10 mg) was dissolved into 2 ml of 0.5M NaCl, and succinyl-Ala-Ala-Pro-phe-4-nitroanilide (substrate, 10 mg) was dissolved into 0.5M NaCl. Due to the cleavage of phe- and nitroanilide, the ratio, R, of the absorbances at 375 nm (reacted substrate) to 320 nm (unreacted substrate) varies with the oxidation states of SPAN, i.e. the pH of the solution. For sulfonated polyaniline held at 0.30 V, 0.10 V and −0.2 V vs Ag for 20 minutes reaction time, R was determined to be 1.36, 1.26, and 0.94, respectively, indicating that the reactivity of the chymotrypsin enzyme is affected by the change of pH.

We claim:

1. A method for sensing the pH of a medium in the vicinity of a sensing electrode, which comprises the steps of:
   (a) placing a hydroxylated polyaniline or sulfonated polyaniline (SPAN) electrode and a counter-electrode in said medium; and
   (b) monitoring an indicia of said hydroxylated polyaniline or SPAN correlative with the pH of said medium.

2. The method of claim 1 wherein said indicia is one or more of electrical potential relative to a reference electrode, conductivity of said electrode, or color of said electrode.

3. The method of claim 1 wherein an electrode is coated with said hydroxylated polyaniline or SPAN.

4. The method of claim 1 wherein said reference electrode and said counter-electrode are the same.

5. The method of claim 1 wherein said hydroxylated polyaniline or SPAN can be represented by the following formula:

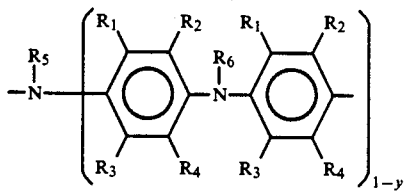

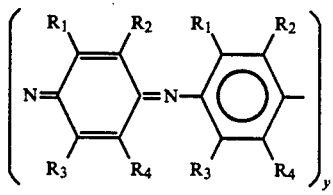

wherein $0 \leq y \leq 1$; $R_1$, $R_2$, $R_3$, $R_4$, $R_5$, and $R_6$ independently are selected from the group consisting of —H, —SO$_3$—, —SO$_3$ H, —R$_7$SO$_3$—, —OCH$_3$, —CH$_3$, —C$_2$H$_5$, —F, —CL, —Br, —I, —(NR$_7$)$_2$, —NHCOR$_7$, —OH, —R$_7$OH, —O—, —SR$_7$, —OR$_7$, —OCR$_7$, —NO$_2$, —COOH, —COOR$_7$, —CHO, and —CN, wherein R$_7$ is a C$_1$-C$_8$ alkyl, aryl or aralkyl group, and wherein the friction of rings containing at least one R$_1$, R$_2$, R, R$_3$, or R$_4$ group being an , —SO$_3$—, —SO$_3$H, —R$_7$SO$_3$—, or —R$_7$SO$_3$H group, or an —OH group or an —R$_7$OH group, varies from approximately 20% to 100%.

6. The method of claim 1 wherein said electrode is a SPAN electrode.

7. A method for modulating the pH of a medium in the vicinity of a sensing electrode, which comprises the steps of:
(a) placing a hydroxylated polyaniline or sulfonated polyaniline (SPAN) electrode in said medium; and
(b) applying a voltage to said electrode to controllably emit or absorb protons from said electrode to modulate the pH of said medium in the vicinity of said electrode.

8. The method of claim 7 wherein an electrode is coated with said hydroxylated polyaniline or SPAN.

9. The method of claim 7 wherein said electrode is a SPAN electrode.

10. The method of claim 7 wherein said hydroxylated polyaniline or SPAN can be represented by the following formula:

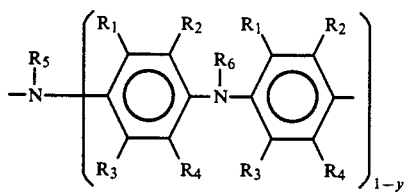

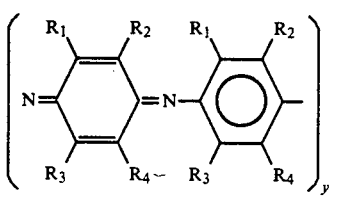

wherein $0 \leq y \leq 1$; $R_1$, $R_2$, $R_3$, $R_4$, $R_5$, and $R_6$ independently are selected from the group consisting of —H, —SO$_3$—, —SO$_3$ H, —R$_7$SO$_3$—, —OCH$_3$, —CH$_3$, —C$_2$H$_5$, —F, —CL, —Br, —I, —(NR$_7$)$_2$, —NHCOR$_7$, —OH, —R$_7$OH, —O—, —SR$_7$, —OR$_7$, —OCR$_7$, —NO$_2$, —COOH, —COOR$_7$, —CHO, and —CN, wherein R$_7$ is a C$_1$-C$_8$ alkyl, aryl or aralkyl group, and wherein the fraction of rings containing at least one R$_1$, R$_2$, R, R$_3$, or R$_4$ group being an —SO$_3$—SO$_3$H, —R$_7$SO$_3$, Or —R$_7$SO$_3$H group, or an —OH group or —R$_7$OH group, varies from approximately 20% to 100%.

11. The method of claim 7 wherein said voltage ranges from between about −0.4 and +1.0 V with respect to a Ag/AgCl reference electrode.

12. The method of claim 1 1 wherein said voltage ranges from between about −0.2 and +0.5 V with respect to a Ag/AgCl reference electrode.

13. A method for sensing the activity/state of a biosensor/catalyst where said activity/state is correlative with pH, which comprises the steps of:
(a) associating the biosensor/catalyst with a hydroxylated polyaniline or sulfonated polyaniline (SPAN) electrode in contact with a medium; and
(b) monitoring an indicia of said hydroxylated polyaniline or SPAN correlative with pH which is correlative with the activity/state of one or more of said biosensor/catalyst, a substrate affected by said biosensor/catalyst, or a substrate which affects said biosensor/catalyst 14. The method of claim 13 wherein said hydroxylated polyaniline or SPAN indicia is one or more of electrical potential relative to a reference electrode, conductivity of said electrode, or color of said electrode.

15. The method of claim 13 wherein an electrode is coated with said hydroxylated polyaniline or SPAN.

16. The method of claim 13 wherein said electrode is a SPAN electrode.

17. The method of claim 13 wherein said hydroxylated polyaniline or SPAN can be represented by the following formula:

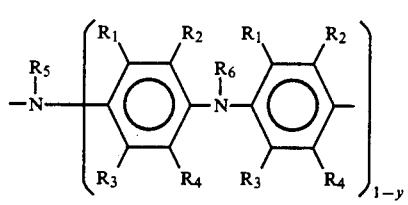

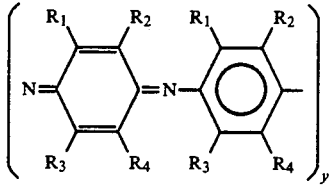

wherein $0 \leq y \leq 1$; $R_1$, $R_2$, $R_3$, $R_4$, $R_5$, and $R_6$ independently are selected from the group consisting of —H, —SO$_3$—, —SO$_3$ H, —R$_7$SO$_3$—, —OCH$_3$, —CH$_3$, —C$_2$H$_5$, —F, —CL, —Br, —I, —(NR$_7$)$_2$, —NHCOR$_7$, —OH, —R$_7$OH, —O—, —SR$_7$, —OR$_7$, —OCR$_7$, —NO$_2$, —COOH, —COOR$_7$, —CHO, and —CN, wherein R$_7$ is a C$_1$-C$_8$ alkyl, aryl or aralkyl group, and wherein the fraction of rings containing at least one R$_1$, R$_2$, R, R$_3$, or R$_4$ group being an —SO$_3$—SO$_3$H, —R$_7$SO$_3$, Or —$R_7SO_3H$ group, or an —OH group or —$R_7OH$ group, varies from approximately 20% to 100%.

18. The method of claim 10 wherein said biosensor/catalyst comprises an enzyme.

19. A method for controlling the activity/state of a biosensor/catalyst where said activity/state is correlative with pH, which comprises the steps of:

(a) associating the biosensor/catalyst with a hydroxylated polyaniline or sulfonated polyaniline (SPAN) electrode in contact with a medium; and (b) applying a voltage to said electrode to controllably emit or absorb protons from said electrode to control the activity/state of said biosensor/catalyst.

20. The method of claim 19 wherein an electrode is coated with said hydroxylated polyaniline or SPAN.

21. The method of claim 19 wherein said electrode is a SPAN electrode.

22. The method of claim 19 wherein said hydroxylated polyaniline or SPAN can be represented by the following formula:

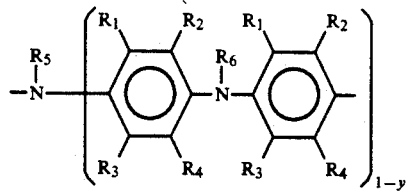

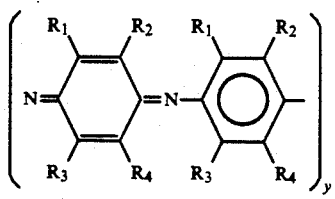

wherein $0 \leq y \leq 1$; $R_1$, $R_2$, $R_3$, $R_4$, $R_5$, and $R_6$ independently are selected from the group consisting of —H, —$SO_3-$, —$SO_3H$, —$R_7SO_3-$, —$OCH_3$, —$CH_3$, —$C_2H_5$, —F, —CL, —Br, —I, —$(NR_7)_2$, —$NHCOR_7$, —OH, —$R_7OH$, —O—, —$SR_7$, —$OR_7$, —$OCR_7$, —$NO_2$, —COOH, —$COOR_7$, —CHO, and —CN, wherein $R_7$ is a $C_1$-$C_8$ alkyl, aryl or aralkyl group, and wherein the fraction of rings containing at least one $R_1$, $R_2$, R, $R_3$, or $R_4$ group being an —$SO_3$—$SO_3H$, —$R_7SO_3$, Or —$R_7SO_3H$ group, or an —OH group or —$R_7OH$ group, varies from approximately 20% to 100%.

23. The method of claim 19 wherein said voltage ranges from between about −0.4 and +1.0 V with respect to Ag/AgCl reference electrode.

24. The method of claim 23 wherein said voltage ranges from between about −0.2 and +0.5 V with respect to a Ag/AgCl reference electrode.

25. The method of claim 19 wherein said biosensor/catalyst comprises an enzyme.

* * * * *